US00PP27037P3

(12) United States Plant Patent
Korlipara

(10) Patent No.: US PP27,037 P3
(45) Date of Patent: Aug. 9, 2016

(54) ***LEUCANTHEMUM* PLANT NAMED 'LUNA'**

(50) Latin Name: *Leucanthemum×superbum*
Varietal Denomination: Luna

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 44 days.

(21) Appl. No.: 14/544,494

(22) Filed: Jan. 13, 2015

(65) Prior Publication Data

US 2016/0205849 P1 Jul. 14, 2016

(51) Int. Cl.
*A01H 5/02* (2006.01)

(52) U.S. Cl.
USPC ..... Plt./285

(58) Field of Classification Search
USPC ..... Plt./285
CPC ..... A01H 5/025
See application file for complete search history.

(56) References Cited

PUBLICATIONS http://www.newplantsandflowers.com/showy-pom-pom-type-leucanthemum/; Oct. 16, 2014; 2 pages.*

* cited by examiner

*Primary Examiner* — Kent L Bell
(74) *Attorney, Agent, or Firm* — Klarquist Sparkman, LLP

(57) ABSTRACT

A new and distinct *Leucanthemum* plant named 'Luna' characterized by showy, double, pom-pom type inflorescences, yellow ray florets that stay yellow, excellent bloom size, a low, compact habit, and excellent vigor.

2 Drawing Sheets

Botanical denomination: *Leucanthemum×superbum.*
Variety designation: 'Luna'.

BACKGROUND OF THE INVENTION

The present invention relates to a new and distinct cultivar of *Leucanthemum* and given the cultivar name 'Luna'. *Leucanthemum* is in the family Asteraceae. This new cultivar originated from a controlled cross between unnamed, proprietary *Leucanthemum×superbum* seedlings. This was part of a controlled breeding program to get a long-lasting yellow flowering *Leucanthemum.*

Compared to the seed parent, the new cultivar has double rather than single inflorescences.

Compared to the pollen parent, the new cultivar has yellow rather than white inflorescences.

Compared to *Leucanthemum×superbum* 'Goldfinch', U.S. Plant Pat. No. 24,499, the new cultivar has inflorescences that are fully double rather than semi-double.

Compared to *Leucanthemum×superbum* Gold Rush™ 'Leukal', U.S. Plant Pat. No. 15,204, the new cultivar has broader ray florets, a shorter habit, and the inflorescence is more yellow, and the inflorescences are fully double rather than semi-double.

SUMMARY OF THE INVENTION

This new *Leucanthemum* cultivar is distinguished as unique with its:

1. showy, double, pom-pom type inflorescences,
2. yellow ray florets that stay yellow,
3. excellent bloom size,
4. a low, compact habit, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a two-year-old plant of the new cultivar growing in full sun in the trial field in mid-June in Canby, Oreg.

FIG. 2 shows a close up of the inflorescences.

FIG. 3 shows the same plant in bud in early June.

FIG. 4 shows the same plant in late June.

DETAILED PLANT DESCRIPTION

The following is a detailed description of the new *Leucanthemum* cultivar based on observations of two-year-old specimens growing in the trial field in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition, 2007.

Plant:

*Type*.—Herbaceous perennial.

*Hardiness*.—USDA Zones 5 to 9.

*Size*.—50 cm wide and 67 cm tall to top of inflorescences.

*Form*.—Basal clump.

*Number of crowns*.—About 80.

*Vigor*.—Excellent.

Stem (flowering):

*Type*.—Ascending, 1 to 3 branches per stem.

*Size*.—Grows to about 48 cm tall to a terminal inflorescence and 8.5 mm wide at base.

*Internode length*.—2 cm to 3 cm.

*Surface texture*.—Pubescent.

*Color*.—Yellow Green 147B.

Leaf:

*Type*.—Simple.

*Shape*.—Lanceolate.

*Arrangement*.—Alternate.

*Blade size*.—Grows to 10 cm long and 31 mm wide.

*Margins*.—Coarsely serrate.

*Petiole*.—Sessile.

*Apex*.—Acute.

*Base*.—Clasping.

*Surface texture*.—Pubescent on both sides.

*Venation*.—Pinnate, main vein top and bottom side Yellow Green 147C.

*Color*.—Topside Yellow Green 137A, bottom side Yellow Green 147B.

Inflorescence:

*Type*.—Composite in style of pompom on terminal stalked heads.

*Number of inflorescences per plant*.—About 80 in first and main flush.

*Size*.—Grows to 7.3 cm wide and 4 cm deep.

*Form*.—Flattened ball; ray florets are held upright on top, horizontally in middle and are reflexed on the bottom half of the inflorescence; mature disc is flat and somewhat visible in a mature inflorescence.

*Peduncle*.—Grows to 9 cm long and 7 mm wide under inflorescence, pubescent, Yellow Green 147B.

*Bud/immature inflorescence*.—2 cm wide and 1.5 cm deep, ovoid, ray florets held vertically and cupped inwards, Yellow Green 147B at phyllaries and Green Yellow 1A to Yellow 5A at ray florets.

*Ray florets*.—With 1 pistil and no stamen, about 240 in number (and about 40 smaller in size near the disc florets), average size 30 mm long and 12 mm wide, corolla limb oblanceolate, average size 23 mm long, to 10 mm wide, tip retuse and 4 to 5 lobed with 1 to two lateral lobes cut to base and strap-shaped (to 23 mm long and 3 mm wide, ligulate with acute tips), tips curl back, margins entire, bases attenuate, glabrous on both sides; top and bottom side Yellow 8A blending to Yellow 8B on the apex, maturing to White NN155A with tip Yellow 8B, pistil 8 mm long, ovary 2 mm long, Yellow Green 145D, style 4 mm long, Green Yellow 1D, 2 branched stigma 0.5 mm long, Yellow 2D.

*Disc*.—Slightly concave becoming slightly convex, becoming 10 mm deep and 20 mm wide with maturity, Yellow 12A.

*Disc florets*.—About 260 in number, each 9 mm long and 2 mm wide; corolla tubular, 5.5 mm long and 2 mm wide, 5 lobed, tips acute, margins entire, glabrous inside and out, Yellow 12A on top blending to Yellow Green 138C on the bottom inside and out; pistil 1, 9 mm long, ovary 3 mm long and Yellow Green 145D, style 5 mm long, Yellow Green 145D, 2 branched stigma 1 mm long, Yellow Orange 15B tinted Brown 200A; stamen 5 in number, 4 mm long, filaments 2 mm long, Yellow Green 150D, anthers 2 mm long, Yellow Green 145D tinted Brown 200A, pollen none.

*Phyllaries*.—About 80 in number, in 3 imbricate whorls, area 3 cm wide and 8 mm deep, lobes lanceolate in shape, grow to 8 mm long and 3 mm wide, Green 137B with margin membranous, entire, and Greyed Purple 187A, tip acute, bases adnate, pubescent outside and glabrous inside.

*Receptacle*.—Grows to 22 mm wide and 7 mm deep, Yellow Green 145A.

*Bloom period*.—June through July in Canby, Oreg.

*Fragrance*.—None.

*Lastingness*.—Each inflorescence lasts about three weeks in Canby, Oreg.

Seeds: None seen.

*Fertility*.—Low.

Disease and pests: The new cultivar is typical to the genus. No known resistances to pests or diseases. No problems have been found in Canby, Oreg.

I claim:

1. A new and distinct *Leucanthemum* plant as herein illustrated and described.

* * * * *

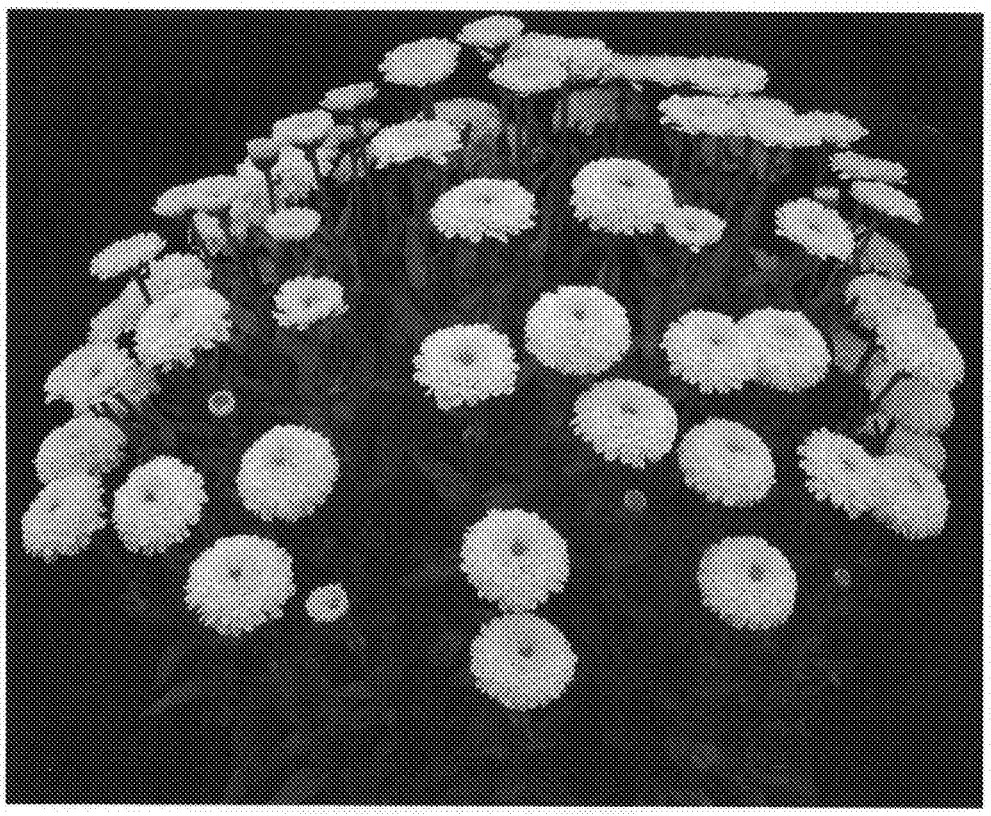
FIG. 1 above,
FIG. 2 on right
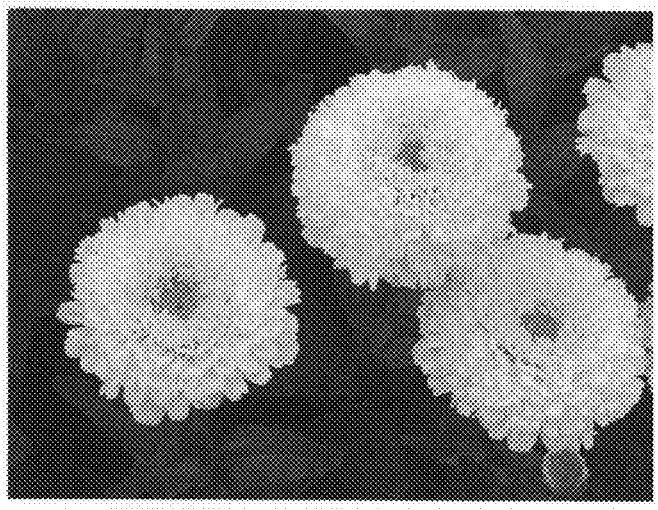

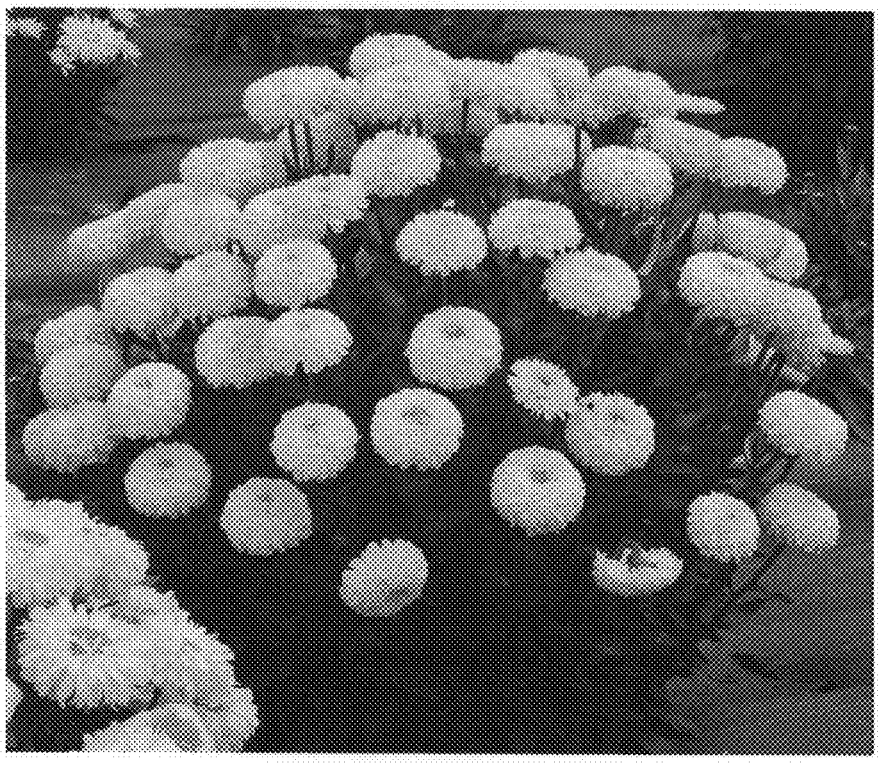

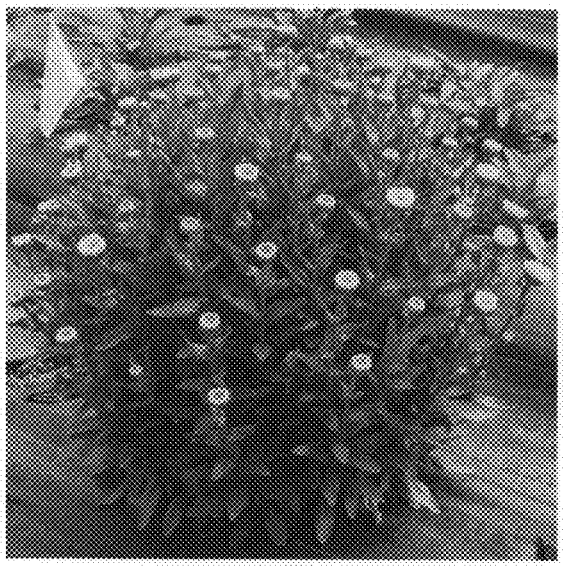
FIG. 3 on left
FIG. 4 below